US007718812B2

(12) United States Patent
Hof

(10) Patent No.: US 7,718,812 B2
(45) Date of Patent: May 18, 2010

(54) PROCESS FOR THE PREPARATION OF 2-(6-SUBSTITUTED-1,3-DIOXANE-4-YL) ACETIC ACID DERIVATES

(75) Inventor: Robert Patrick Hof, Panningen (NL)

(73) Assignee: AstraZeneca UK Limited, London (GB)

(*) Notice: Subject to any disclaimer, the term of this patent is extended or adjusted under 35 U.S.C. 154(b) by 486 days.

(21) Appl. No.: 10/501,250

(22) PCT Filed: Dec. 9, 2002

(86) PCT No.: PCT/NL02/00876

§ 371 (c)(1),
(2), (4) Date: Dec. 6, 2004

(87) PCT Pub. No.: WO03/059901

PCT Pub. Date: Jul. 24, 2003

(65) Prior Publication Data
US 2005/0090674 A1 Apr. 28, 2005

(30) Foreign Application Priority Data
Dec. 27, 2001 (EP) .................. 01000794

(51) Int. Cl.
C07D 319/06 (2006.01)
(52) U.S. Cl. .................. 549/333; 549/375
(58) Field of Classification Search ........ 549/333, 549/375
See application file for complete search history.

(56) References Cited

U.S. PATENT DOCUMENTS

| 3,992,432 | A | 11/1976 | Napier et al. |
| 5,278,313 | A | 1/1994 | Thottathil et al. |
| 5,594,153 | A | 1/1997 | Thottathil et al. |
| 6,278,001 | B1 | 8/2001 | Solladie et al. |
| 6,784,171 | B2 | 8/2004 | Taylor et al. |
| 6,844,437 | B1 | 1/2005 | Taylor et al. |
| 6,870,059 | B2 | 3/2005 | Kooistra et al. |
| 2006/0040898 | A1 | 2/2006 | Puthiaparampil et al. |

FOREIGN PATENT DOCUMENTS

| EP | 0563401 | 10/1993 |
| EP | 0627421 | 12/1994 |
| EP | 1 024 139 A1 | 8/2000 |
| GB | 885516 | 12/1961 |
| JP | 58-164546 | 9/1983 |
| JP | 4-266879 | 9/1992 |
| JP | 5-112492 | 5/1993 |
| JP | 6-340630 | 12/1994 |
| JP | 10-158199 | 6/1998 |
| WO | WO-91/13876 | 9/1991 |
| WO | WO 93/08823 | 5/1993 |
| WO | WO 97/19917 | 6/1997 |
| WO | WO-00/08011 | 2/2000 |
| WO | WO 00/49014 | 8/2000 |
| WO | WO-00/68221 | 11/2000 |
| WO | WO 01/72706 | 10/2001 |
| WO | WO 01/85975 | 11/2001 |
| WO | WO-02/06266 A1 | 1/2002 |
| WO | WO 03/006439 | 1/2003 |
| WO | WO-03/106447 A1 | 12/2003 |
| WO | WO 2004/014872 | 2/2004 |
| WO | WO 2004/054986 | 7/2004 |
| WO | WO 2004/108691 | 12/2004 |
| WO | WO 2004/113314 | 12/2004 |
| WO | WO 2005/023779 | 3/2005 |
| WO | WO 2005/028450 | 3/2005 |
| WO | WO 2005/042522 | 5/2005 |
| WO | WO 2006/067456 | 6/2006 |

OTHER PUBLICATIONS

Naik et al., Am. Inst. Chem. Eng. J. (1984), vol. 44(3), pp. 612-646.*
Advanced Organic Chemistry, Reactions, Mechanisms and Structure, p. 392 (1992).
Barry et al., "Alkylations en Absence de Solvant Organique. Effects D'addition D'oxydes Mineraux et de sels D'Ammonium—II," Tetrahedron 39(16):2673-2677 (1983).
Barry et al., "Easy and Efficient Anion Alkylations in Solid-Liquid PTC Conditions," Tetrahedron Letters 23(51):5407-5408 (1982).
Bennett et al., "Methyl (3R)-3-Hydroxyhex-5-enoate as a Precursor to Chiral Mevinic Acid Analogues," J. Chem. Soc. 1:133-140 (1991).
Bram et al., "Anionic Activation by Solid-Liquid Phase Transfer Catalysis Without Solvent: An Improvement in Organic Synthesis," Israel Journal of Chemistry 26:291-298 (1985).
Chikara et al., "Preparation of Optically Active 5,6-epoxyhexanoic Acid Esters as Materials for Physiologically Active Substances," Chemical Abstracts 118(11) (1993).
Halpern, "Choosing a Phase-Transfer Catalyst for the First Experiment," Phase-Transfer Catalysis Communications 3(1):1-16 (1997).
Murphy et al., "Chemistry of Cephalosporin Antibiotics. XVII. Synthesis of 7-Acyl-3-methyl-2-cephern-4-carboxylic Acid Esters," J. Org. Chem. 35(7):2429 (1970).
Sakaki et al., "Lipase-catalyzed Asymmetric Synthesis of 6-(3-Chloro-2-hydroxypropyl)-1,3-dioxin-4-ones and Their Conversion to Chiral 5,6-Epoxyhexanoates," Tetrahedron: Asymmetry 2(5):343-346 (1991).

(Continued)

Primary Examiner—Taofiq A Solola
(74) Attorney, Agent, or Firm—Morgan, Lewis & Bockius LLP

(57) ABSTRACT

The invention relates to a process for the conversion of group X in a 2-(6-substituted)-1,3-dioxane-4yl) acetic acid derivative according to formula 2 into a group OY in the presence of a phase transfer catalyst and an oxylating agent, by using as a phase transfer catalyst a quarternary phosphonium ion and by using as an oxylating agent an OY-ion. X stands for a halogen and R1, R2 and R3 are each independently a C1–4 alkylgroup or R1 and R2 together with the C-atom to which they are bound form a 5- or 6-membered cycloalkyl; Y stands for RA-CO— or for RB—SO2- with RA, RB are chosen from the group of alkyl or aryl with 1–12 C-atoms.

8 Claims, No Drawings

OTHER PUBLICATIONS

Starks et al., "Phase Transfer Catalysis, Principles and Techniques," pp. 140-169 (1978).

March, Advanced Organic Chemistry: Reactions, Mechanisms, and Structure, 4th ed., John Wiley & Sons, Inc, p. 378 (1992).

Menges et al. "Oxidative Degradation of γ-Butyrolactons into 1,3-Diols via a Criegee Rearrangement of Peroxosulfonates. An Enantioselective Synthesis of Compactin Lactone and its Diastereomer" Synlett 12:901-905 (1993).

Morrison and Boyd "Alkaline hydrolysis of esters" Lehrbuch der Organischen Chemie, 2nd ed., Verlag Chemie, p. 739 (1978) (Translation enclosed).

Presentation given at the 20th International Congress of Heterocyclic Chemistry in Palermo, Aug. 1-5, 2005.

Presentation given at the Gordon Conference on Heterocyclic Compounds, Salve Regina University, Newport, Rhode Island, Jul. 4-9, 2004.

Shao et al. "Asymmetric hydrogenation of 3,5-Dioxoesters catalyzed by Ru-binap complex: A short step asymmetric synthesis of 6-substituted 5,6-dihydro-2-pyrones" Tetrahedron 49(10):1997-2010 (1993).

Murai et al. "Catalytic effect of tertiary amines on the esterification reaction of potassium acetate and butyl bromide" Journal of the Chemical Society of Japan 5:805-810 (1982) (Translation enclosed).

\* cited by examiner

PROCESS FOR THE PREPARATION OF 2-(6-SUBSTITUTED-1,3-DIOXANE-4-YL) ACETIC ACID DERIVATES

RELATED APPLICATIONS

This application is a national stage filing under 35 U.S.C. 371 of International Application PCT/NL02/00876, filed Dec. 9, 2002, which claims priority from United Kingdom Application No. 01000794.6, filed Dec. 27, 2001, the specifications of each of which are incorporated by reference herein. International Application PCT/NL02/00876 was published under PCT Article 21(2) in English.

The invention relates to a process for the preparation of a 2-(6-substituted-1,3-dioxane-4-yl) acetic acid derivative according to formula 1,

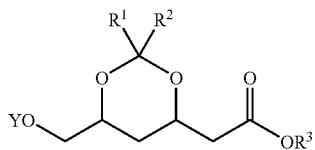

(1)

wherein $R^1$, $R^2$ and $R^3$ are each independently a C1–4 alkyl-group or wherein $R^1$ and $R^2$ together with the C-atom to which they are bound form a 5- or 6-membered cycloalkyl and wherein Y stands for $R^A$—CO— or for $R^B$—SO$_2$— with $R^A$, $R^B$ are chosen from the group of alkyl or aryl with 1–12 C-atoms, from its corresponding 2-(6-substituted-1,3-dioxane-4-yl) acetic acid derivative according to formula 2,

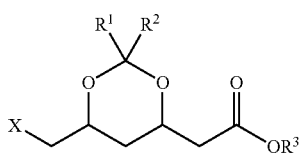

(2)

wherein $R^1$, $R^2$ and $R^3$ are as defined above and wherein X stands for a halogen, in the presence of a phase transfer catalyst and an oxylating agent.

Such a process is known from EP 1 024 139, wherein the preparation of a compound according to formula 1 from a compound according to formula 2 is achieved in the presence of a quaternary ammonium salt (phase transfer catalyst) and a carboxylic acid salt (acyloxylating agent).

It is the object of the invention to provide an alternative process for the preparation of a 2-(6-substituted-1,3-dioxane-4-yl) acetic acid derivative according to formula 1 from its corresponding 2-(6-substituted-1,3-dioxane-4-yl) acetic acid derivative according to formula 2.

This is achieved according to the invention by using a quarternary phosphonium ion according to formula 3 as a phase transfer catalyst,

(3)

wherein $R^4$, $R^5$, $R^6$, $R^7$ each independently stand for an alkyl, cycloalkyl, aralkyl or aryl with 1 to 12 C-atoms, and an ion according to formula 4,

OY⁻ (4)

wherein Y is as defined above, as an oxylating agent. The reaction has a high yield.

The quarternary phosphonium ion according to formula 3 used as a phase transfer catalyst and the ion according to formula 4 used as an oxylating agent may be present in a quarternary phosphonium salt according to formula 5,

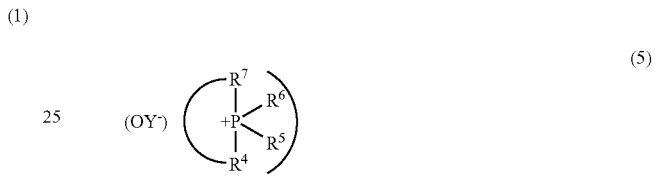

(5)

wherein Y, $R^4$, $R^5$, $R^6$ and $R^7$ are as defined above. The phosphonium salt according to formula 5 can be used as both a phase transfer catalyst and as an oxylating agent. The quarternary phosphonium salt according to formula 5 can be prepared according to methods known to the person skilled in the art (e.g. analogous to the preparation of tetra-n-butylammoniumacetate as described in U.S. Pat. No. 5,278,313).

In a preferred embodiment of the invention, the phase transfer catalyst and the oxylating agent are not present in the same molecule. In this embodiment, a quarternary phosphonium salt according to formula 3a,

(3a)

wherein $R^4$, $R^5$, $R^6$ and $R^7$ are as defined above and wherein A stands for the anion of the quarternary phopshoniumsalt and is selected from the group of halogens, for example Cl, Br, I is used as a phase transfer catalyst and the acid salt according to formula 4a,

(OY⁻)$_n$M$^{n+}$ (4a)

wherein Y is as defined above, wherein M stands for alkali metal or an alkaline metal, for example Li, K, Na, Mg, Ca, Ba and wherein n represents an integer of 1 or 2, depending on the valence of M is used as an oxylating agent. Preferred is M is K or Na.

In the process according to the invention, halogens X are preferably Cl, Br or I, more preferably Cl.

In the process according to the invention, $R^1$, $R^2$ and $R^3$ are preferably a C1–4 alkyl group, more preferably $R^1$ and $R^2$ are a methyl or an ethyl group, more preferably a methyl group. $R^3$ is preferably a methyl or a butyl, most preferably a t-butyl.

In the process according to the invention Y groups are preferably represented by $R^A$—CO— or $R^B$—SO$_2$—, wherein $R^A$, $R^B$ are chosen from the group of C$_{1-C4}$ alkyl or aryl with 6–10 C-atoms. In a preferred embodiment, Y is chosen from the group of acyl, more preferably acetyl (with $R^A$ is CH$_3$), benzenesulfonyl (with $R^B$ is benzene), more preferably nitro substituted benzenesulfonyl (with $R^B$ is p-nitrobenzene), tosyl (with $R^B$ is p-methyl-benzene) or mesyl (with $R^B$ is methyl).

In the process according to the invention, preferably a phosphonium salt according to formula 3a or according to formula 5, with at least three out of four R groups are the same (e.g. $R^4$, $R^5$, $R^6$ are butyl and $R^7$ is methyl or $R^4$, $R^5$, $R^6$ are phenyl and $R^7$ is butyl), more preferably a phosphonium salt with all four R groups are the same, is used.

$R^A$ and $R^B$ and $R^4$, $R^5$, $R^6$, $R^7$, —in case $R^4$, $R^5$, $R^6$, $R^7$ are aryl or aralkyl-, may be substituted for example with substituents chosen from the group of halogens, alkoxy (e.g. methoxy or ethoxy) with 1–6 C-atoms, alkyl with 1–6 C atoms, (e.g. methyl if $R^B$ is toluene) or nitro, preferably only $R^A$ or $R^B$ are substituted.

The quarternary phosphonium salt according to formula 3a is preferably used in a molar equivalent amount of 0.01 to 1.0, more preferably 0.05 to 0.7, most preferably 0.1 to 0.5 relative to the amount of compound according to formula 2.

The quarternary phosphonium salt according to formula 5 is preferably used in a molar equivalent amount of 0.8 to 5, preferably 1 to 3, most preferably 1 to 1.5.

The acid salt according to formula 4a is preferably used in a molar equivalent amount of 1 to 5 relative to the amount of compound according to formula 2 present. More preferably, a molar equivalent amount of acid salt according to formula 4a of 1 to 4, most preferably 2 to 3, is used.

The solvents suitable for use in the present invention are a various number of organic solvents, which are known to the person skilled in the art. Organic solvents, which may be used are hydrocarbon series solvents, for example benzene, toluene, cyclohexane, etc.; ether series solvents, for example diethyl ether tetrahydrofuran, 1,4-dioxane, methyl-t-butyl ether, dimethoxyethane, etc.; ester series solvents, for example ethyl acetate, butyl acetate, etc.; halogen containing solvents, for example methylene chloride, chloroform, 1,1,1-trichloroethane, etc.; nitrogen-containing solvents, for example acetamide, formamide, acetonitrile etc.; and aprotic polar solvents, for example dimethyl sulfoxide, N,N-dimethylformamide, N-methylpyrrolidone, hexamethylphosphoric triamide etc. Preferably, the solvent used is an aprotic polar solvent, more preferably the solvent used is N-methylpyrrolidone or N,N-dimethylformamide. The solvent can be used alone or in combination with one or more other solvent species, for example N-methylpyrrolidone in combination with toluene.

The temperature, by which the process of the invention is preferably carried out, is between 80 and 200° C., more preferably between 100 and 160° C., most preferably between 110 and 150° C.

The reaction product can be isolated from the reaction medium, if desired, according to methods known to the person skilled in the art (e.g. the method as described in U.S. Pat. No. 5,278,313).

The invention will be illustrated by way of the following examples. However, these examples are not meant to restrict the invention.

EXAMPLES

Example 1

0.5 molar equivalents tetrabutylphosphoniumbromide (TBPB) and 2.5 molar equivalents potassiumacetate were added to a solution of I (tert-butyl 2-[(4R,6S)-6-(chloromethyl)-2,2-dimethyl-1,3-dioxan-4-yl]acetate) in the solvent N-methlpyrrolidone (1 g/3 ml) at 100° C. The conversion of I in the presence of TBPB was 87.6% after 20 hours reaction time, the conversion of I into II (tert-butyl 2-{(4R,6S)-2,2-dimethyl-6-[(methyl-carbonyloxy)methyl]-1,3-dioxan-4-yl}acetate) thereof being 90.3%.

Example 2

Example I was repeated whereby the reaction temperature for the conversion of I into II was kept at 115° C. The conversion of I in the presence of TBPB was 95.1% after 3 hours reaction time, the conversion of I into II thereof being 91%.

Example 3

0.1 molar equivalents tetraphenylphosphoniumbromide (TTB) and 2.5 molar equivalents potassiumacetate were added to a solution of I (tert-butyl 2-[(4R,6S)-6-(chloromethyl)-2,2-dimethyl-1,3-dioxan-4-yl]acetate) in the solvent N-methylpyrrolidone (1 g/3 ml) at 140° C. After 20 hours, the conversion of I was 97%, the conversion of I into II thereof being 77.2%.

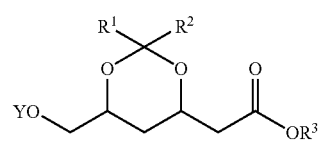

Formula 1

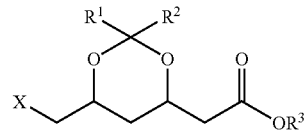

Formula 2

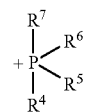

Formula 3

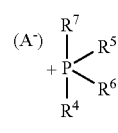

Formula 3a

-continued $$OY^-  \quad (4)$$
Formula 4

$$(OY^-)_n \ M^{n+} \quad (4a)$$
Formula 4a

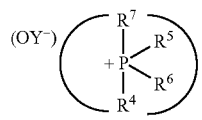 (5)

Formula 5

The invention claimed is:

1. Process for the preparation of a 2-(6-substituted-1,3-dioxane-4-yl) acetic acid derivative according to formula 1,

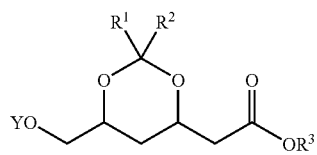 (1)

wherein $R^1$, $R^2$ and $R^3$ are each independently a C1–4 alkyl group or wherein $R^1$ and $R^2$ together with the C-atom to which they are bound form a 5- or 6-membered cycloalkyl and Y stands for $R^A$—CO— or for $R^B$—SO$_2$— where $R^A$, $R^B$ are chosen from the group of alkyl or aryl with 1–12 C-atoms, from its corresponding 2-(6-substituted-1,3-dioxane-4-yl) acetic acid derivative according to formula 2,

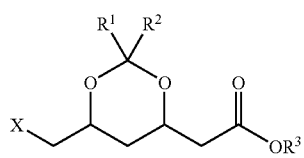 (2)

wherein $R^1$, $R^2$ and $R^3$ are as defined above and X stands for a halogen, in the presence of a phase transfer catalyst and an oxylating agent, characterized in that a quarternary phosphonium ion according to formula 3,

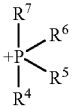 (3)

wherein $R^4$, $R^5$, $R^6$, $R^7$ each independently stand for an alkyl, cycloalkyl, aralkyl or aryl with 1 to 12 C-atoms, is used as a phase transfer catalyst and an ion according to formula 4, $$OY^- \quad (4)$$

wherein Y is as defined above, is used as an oxylating agent.

2. Process according to claim 1, characterized in that $R^A$, $R^B$ are chosen from the group of $C_1$–$C_4$ alkyl or aryl with 6–10 C-atoms.

3. Process according to claim 1, characterized in that as a phase transfer catalyst a quarternary phosphonium salt according to formula 3a,

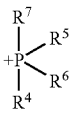 (3a)

wherein $R^4$, $R^5$, $R^6$ and $R^7$ are as defined above and A stands for a halogen, is used and in that an acid salt according to formula 4a, $$(OY^-)_n M^{n+} \quad (4a)$$

wherein Y is as defined above and, M stands for alkali metal or an alkaline metal, is used as an oxylating agent.

4. Process according to claim 3, characterized in that the quarternary phosphonium salt according to formula 3a is used in a molar equivalent amount of 0.05 to 0.7 relative to the amount of compound according to formula 2.

5. Process according to claim 4, characterized in that the quarternary phosphonium salt according to formula 3a is used in a molar equivalent amount of 0.1 to 0.5 relative to the amount of compound according to formula 2.

6. Process according to any of claims 1-5, characterized in that the process is carried out at a temperature between 100 and 160° C.

7. Process according to any of claims 1-5, characterized in that the process is carried out at a temperature between 110 and 150° C.

8. Process according to any of claims 1-5, characterized in that the compound according to formula 1 is tert-butyl 2-{(4R,6S)-2,2 dimethyl-6-[(methyl-carbonyloxy)methyl]-1,3-dioxan-4-yl}acetate and in that the compound according to formula 2 is tert-butyl 2-[(4R,6S)-6-(chloromethyl)-2,2-dimethyl-1,3-dioxan-4yl]acetate.

* * * * *